(12) United States Patent
Fischer et al.

(10) Patent No.: US 9,492,216 B2
(45) Date of Patent: Nov. 15, 2016

(54) HANDLE FOR AN ABLATION DEVICE

(75) Inventors: Gerald Fischer, Völs (AT); Florian Hintringer, Ampass (AT); Martin Goll, Innsbruck (AT)

(73) Assignee: Afreeze GmbH, Innsbruck (AT)

( * ) Notice: Subject to any disclaimer, the term of this patent is extended or adjusted under 35 U.S.C. 154(b) by 1231 days.

(21) Appl. No.: 12/922,150

(22) PCT Filed: Mar. 12, 2009

(86) PCT No.: PCT/EP2009/001786
§ 371 (c)(1),
(2), (4) Date: Dec. 3, 2010

(87) PCT Pub. No.: WO2009/112262
PCT Pub. Date: Sep. 17, 2009

(65) Prior Publication Data
US 2011/0082453 A1    Apr. 7, 2011

Related U.S. Application Data

(60) Provisional application No. 61/035,847, filed on Mar. 12, 2008.

(51) Int. Cl.
*A61B 18/02* (2006.01)
*A61B 18/14* (2006.01)
(Continued)

(52) U.S. Cl.
CPC .......... *A61B 18/02* (2013.01); *A61B 18/1492* (2013.01); *A61B 18/18* (2013.01); *A61B 18/20* (2013.01); *A61B 2017/00867* (2013.01);
(Continued)

(58) Field of Classification Search
CPC .......... A61B 18/02; A61B 2018/0231; A61B 2018/0091; A61B 2017/0046
USPC ...................................... 606/21, 41
See application file for complete search history.

(56) References Cited

U.S. PATENT DOCUMENTS 5,147,355 A * 9/1992 Friedman ............... A61B 18/02
  606/21
5,327,905 A * 7/1994 Avitall ...................... 600/585
(Continued)

FOREIGN PATENT DOCUMENTS

EP    0 868 922 A2    10/1998
EP    1 042 990 A1    10/2000
(Continued)

OTHER PUBLICATIONS

Communication pursuant to Article 94(3) EPC with Form 2906, corresponding to Application No. 09720316.0; dated Jan. 11, 2012, 4 pages.
(Continued)

*Primary Examiner* — Jocelyn D Ram
(74) *Attorney, Agent, or Firm* — Lewis Roca Rothgerber Christie LLP

(57) ABSTRACT

A handle for an ablation device, the handle comprising a positioning control handle part adapted to be coupled to a positioning catheter of the ablation device and adapted to position the positioning catheter in an object, and an ablation control handle part adapted to be coupled to an ablation catheter of the ablation device and adapted to ablate material of the object using the ablation catheter, wherein the positioning control handle part and the ablation control handle part are adapted to be separable from one another.

18 Claims, 7 Drawing Sheets

(51) Int. Cl.
  *A61B 18/18* (2006.01)
  *A61B 18/20* (2006.01)
  *A61B 17/00* (2006.01)
  *A61B 18/00* (2006.01)

(52) U.S. Cl.
  CPC ............ *A61B2018/00273* (2013.01); *A61B 2018/00279* (2013.01); *A61B 2018/00285* (2013.01); *A61B 2018/00351* (2013.01); *A61B 2018/00375* (2013.01); *A61B 2018/00577* (2013.01); *A61B 2018/00916* (2013.01); *A61B 2018/0212* (2013.01)

(56) References Cited

U.S. PATENT DOCUMENTS

| | | | |
|---|---|---|---|
| 5,599,300 A | 2/1997 | Weaver et al. | |
| 5,766,184 A | 6/1998 | Matsuno et al. | |
| 5,964,753 A * | 10/1999 | Edwards | 606/33 |
| 5,995,875 A * | 11/1999 | Blewett et al. | 607/98 |
| 6,027,497 A * | 2/2000 | Daniel et al. | 606/15 |
| 6,052,607 A * | 4/2000 | Edwards et al. | 600/374 |
| 6,163,716 A * | 12/2000 | Edwards et al. | 600/374 |
| 6,440,126 B1 * | 8/2002 | Abboud et al. | 606/22 |
| 6,640,120 B1 * | 10/2003 | Swanson | A61B 18/1492 600/374 |
| 2001/0021867 A1 * | 9/2001 | Kordis et al. | 607/112 |
| 2002/0111618 A1 | 8/2002 | Stewart et al. | |
| 2003/0204187 A1 | 10/2003 | Hintringer et al. | |
| 2004/0064134 A1 * | 4/2004 | Xiao et al. | 606/21 |
| 2004/0225286 A1 * | 11/2004 | Elliott | 606/41 |
| 2005/0177211 A1 * | 8/2005 | Leung | A61B 18/148 607/101 |
| 2005/0192607 A1 | 9/2005 | Hutchins et al. | |
| 2006/0142694 A1 | 6/2006 | Bednarek et al. | |
| 2006/0253070 A1 | 11/2006 | Butler | |
| 2007/0149961 A1 | 6/2007 | Wittenberger et al. | |
| 2009/0005769 A1 * | 1/2009 | Haywood | 606/21 |
| 2009/0099544 A1 * | 4/2009 | Munrow et al. | 604/506 |
| 2010/0145331 A1 * | 6/2010 | Chrisitian et al. | 606/33 |

FOREIGN PATENT DOCUMENTS

| | | |
|---|---|---|
| EP | 1 182 980 A1 | 3/2002 |
| EP | 1 356 779 A1 | 10/2003 |
| GB | 2145932 A | 4/1985 |
| WO | WO 94/07413 | 4/1994 |
| WO | WO 97/36548 | 10/1997 |
| WO | WO 00/67656 | 11/2000 |
| WO | WO 2006/010908 A1 | 2/2006 |
| WO | WO 2007/028232 A1 | 3/2007 |
| WO | WO 2007/145759 A2 | 12/2007 |

OTHER PUBLICATIONS

Communication pursuant to Article 94(3) EPC issued in parallel European Application No. 09 720 316.0-1659 dated Oct. 22, 2013; 5 pages.
International Search Report, dated Sep. 30, 2009, corresponding to PCT/EP2009/001786.
International Preliminary Report on Patentability, dated Sep. 14, 2010, corresponding to PCT/EP2009/001786, 9 pages.

* cited by examiner

HANDLE FOR AN ABLATION DEVICE

CROSS-REFERENCE TO A RELATED APPLICATION

This application is a National Phase Patent Application of International Patent Application Number PCT/EP2009/001789, filed on Mar. 12, 2009, which claims priority of U.S. Provisional Application No. 61/035,847, filed on Mar. 12, 2008.

This application claims the benefit of the filing date of U.S. Provisional Patent Application No. 61/035,847 filed Mar. 12, 2008, the disclosure of which is hereby incorporated herein by reference.

The invention relates to a handle or grip for an ablation device.

The invention further relates to an ablation device.

Moreover, the invention relates to a method of operating an ablation device.

Cryosurgery is the application of extreme cold to ablate abnormal or diseased tissue. Cryosurgery works by taking advantage of the destructive force of freezing temperatures on cells. At low temperatures, ice crystals may form inside the cells, which can tear them apart. More damage may occur when blood vessels supplying the tissue freeze.

Most ablation devices have the shape of a single elongated member or tube bearing the ablation applicator (electrodes, ultra sound emitter, laser source, cooling tip etc.) on its distal end. In some applications of cryosurgery and cryoablation, two different types of catheters have to be operated simultaneously, namely a positioning catheter provided for appropriately positioning the ablation device in an object and an ablation catheter provided for ablating a specific portion of the object. Such an ablation device comprising a positioning catheter and an ablation catheter in one combined device can be termed a twin catheter. A physician operates the ablation device by means of a handle.

US 2007/0149961 discloses a medical device having a means for actuating a pair of opposing jaw members. The jaw members are movable relative to one another from a first position, wherein the jaw members are disposed in a spaced apart relation relative to one another, to a second position, wherein the jaw members cooperate to grasp tissue therebetween. An ablation mechanism is connected to at least one of the jaws members, such that the jaw members are capable of conducting ablation energy through the tissue grasped therebetween.

EP 1,356,779 discloses a device which has a catheter with a counter bearing device near its distal end for holding the distal end on a cardial vessel opening, a linear ablation applicator arranged on the proximal or distal side of the counter bearing and able to be changed from a stretched passive position to a radially expanded, approximately circular peripheral ablation position.

Twin catheter devices are also described in EP 1,042,990 and EP 1,182,980.

Appropriate handles for single catheter devices are well described in the art. Some examples can be found in WO 2007/145759, WO 2007/028232, US 2006/0253070A1, US 2006/0142694 A1.

It is an object of the invention to enable an efficient handling of an ablation device.

In order to achieve the object defined above, a handle for an ablation device, an ablation device, and a method of operating an ablation device according to the independent claims are provided.

According to an exemplary embodiment of the invention, a handle for an ablation device is provided, the handle comprising a positioning control handle part adapted to be coupled to a positioning catheter of the ablation device and adapted to position the positioning catheter in an object, and an ablation control handle part adapted to be coupled to an ablation catheter of the ablation device and adapted to ablate material of the object using the ablation catheter, wherein the positioning control handle part and the ablation control handle part are adapted to be separable (for instance spatially, mechanically and/or functionally) from one another.

According to another exemplary embodiment of the invention, an ablation device is provided, the ablation device comprising a handle having the above mentioned features, the positioning catheter, and the ablation catheter.

According to still another exemplary embodiment of the invention, a method of operating an ablation device is provided, the method comprising coupling a positioning control handle part to a positioning catheter of the ablation device, operating the positioning control handle part to position the positioning catheter in an object, coupling an ablation control handle part to an ablation catheter of the ablation device, and operating the ablation control handle part to ablate material of the object using the ablation catheter, wherein the positioning control handle part and the ablation control handle part are separable from one another (particularly during the described procedure).

The term "catheter" may particularly denote a tube that can be inserted into a body cavity, duct or vessel. Catheters may thereby allow access by surgical instruments. A catheter may be a flexible tube. In other embodiments, a catheter may be a stiff tube. Its diameter may vary particularly between 0.3 mm and 10 mm.

The term "handle" may particularly denote a grip or hand piece shaped, dimensioned and configured to allow to be operated by a hand or two hands of a physician.

The term "ablation device" may particularly denote any apparatus which is adapted to ablate, deactivate, destroy or remove material, particularly tissue of a physiological object such as a human being or an animal, via the application of an ablation medium such as extreme cold or heat.

The term "adapted to be separated from one another" may particularly denote that the positioning control handle part and the ablation control handle part may be functionally and/or spatially separable, for instance made of two different individual components which are not integrally formed and can be selectively connected to one another or disconnected from one another. This includes the opportunity to reversibly eliminate a coupling between the handle parts or to rigidly couple them to one another which may be realized by adjusting the shapes of the connection position or coupling position of the two handle parts accordingly. It may also include that a spatial arrangement of the positioning control handle part and the ablation control handle part relative to one another is alterable to selective arrange the positioning control handle part and the ablation control handle part at a distance from one another or close to one another. There may or may not be an intermediate piece between the positioning control handle part and the ablation control handle part. Thus, the positioning control handle part and the ablation control handle part may be coupled directly or indirectly. "Adapted to be separated from one another" may also denote that the positioning control handle part and the ablation control handle part may be arranged to be slidable with respect to one another for transforming the system between a retracted state and an extended state.

The term "object" may particularly denote any object under examination, analysis or ablation and may be a human being or an animal. More particularly, it may be an organ of such a physiological object, particularly a heart or a part thereof.

According to an exemplary embodiment of the invention, a two-part handle for an ablation device such as a cryosurgery or cryoablation device may be provided which allows to either connect or disconnect two handle parts for significantly simplifying positioning and ablation procedures occurring in the context of the ablation. Particularly, for positioning the ablation device properly in an object such as a human being, the positioning control handle part (optionally in combination with the ablation control handle part) may be operated accordingly to simplify or make more precisely a positioning procedure. For a subsequent preparation of an ablation procedure, the ablation control handle part (optionally with or without the positioning control handle part) may be operated in a specific manner to simplify or make more precisely a subsequent ablation procedure.

For example, it may be appropriate to connect positioning control handle part and ablation control handle part to one another for positioning, and to subsequently separate (for instance splitting up into two individual pieces or spacing the two still connected parts by an intermediate connector) the two handle parts so that a relative motion between the ablation control handle part and the positioning control handle part may allow for an exact definition of an ablation trajectory or procedure, followed by the application of an ablation medium to the correctly positioned ablation catheter. By taking such a measure, the flexibility and accuracy of the positioning and ablation procedure may be significantly improved.

Next, further exemplary embodiments of the handle will be explained. However, these embodiments also apply to the ablation device and to the method.

The positioning control handle part and the ablation control handle part may be adapted to be operable in a first configuration in which the control handle part and the ablation control handle part may be fixedly connected to one another and may be adapted to be operable in a second configuration in which at least one of the control handle part and the ablation control handle part is operable independently from the other one of the control handle part and the ablation control handle part. Thus, due to the specific adaptation of the two handle parts, a first function may be realized in a combined mode and a second function may be realized in a separated mode. For example, for positioning the catheters within a human body, it may be appropriate to fixedly connect the two handle parts to one another for insertion of a tip of the position catheter at a specific location in the human body, for instance at a physiological or anatomical reference or target position. Upon proper positioning of the catheters, the two handle parts may be separated from one another mechanically and may be moved relative to one another for example to trigger a geometrical shape change of the ablation catheter (for instance from a straight linear configuration to a curved configuration). With such a procedure, the ablation line of the ablation catheter may be positioned exactly at a desired anatomical position which may require for instance folding of this ablation portion which can be triggered by a relative motion of the ablation handle with respect to the position handle. However, it is also possible that, with respect to the previously described configuration, the ablation control handle part and the positioning control handle part change function and/or position so that positioning is performed with the use of only the positioning control handle part, and preparation of the ablation is performed by a combination of both handle parts. In a further configuration, the positioning control handle part is operated alone for positioning, and the ablation control handle part is operated alone for preparing the ablation.

The positioning control handle part and the ablation control handle part may be adapted to be fixedly connectable to one another in a detachable manner. The term "fixedly connectable" may denote that, in a mounted or assembled state, the positioning control handle part and the ablation control handle part essentially form a common handle with rigidly connected components, i.e. a single piece. The "detachable" property may denote that the connection is configured such that, with an easy operation, for instance with one hand movement or maneuver, the two handle parts may be separated from one another. This may allow for an easy construction and a simple operation.

The positioning control handle part and the ablation control handle part may be adapted to be connectable to one another by one of the group consisting of a plug-in connection, a bayonet fitting, a magnetic fitting, a snap-in connection, a screw closure and a form closure. Therefore, positive locking mechanisms and non-positive locking mechanisms may be used to connect the two handle parts in a reversible manner.

The positioning control handle part and the ablation control handle part may comprise a common lumen. For example, both of the positioning control handle part and the ablation control handle part may be formed as hollow cylindrical tubes having a connection portion at which the two handle parts may be assembled (directly or indirectly via an intermediate piece) to form a common lumen. Through this common lumen, a plurality of components may be guided used for both positioning and ablation preparation as well as for performing the ablation. For example, a positioning or guiding wire for the positioning control may be provided within the lumen. Also the provision of contrast agents or flushing solutions may be performed via a supply conduit guided through the common lumen. Regarding the ablation preparation, a mechanical mechanism for converting the ablation catheter from a retracted operation mode into an expanded operation mode may be guided through the common lumen, for instance a taut wire or a push mechanism. The common lumen may also accommodate electrical connections or an ablation medium supply line such as a cooling agent supply line through which a cooling agent such as nitrous oxide ($N_2O$) can be guided from a container towards the ablation element for ablating the material by shock cooling. Such a refrigerant or coolant may be a compound used in a cooling procedure or cycle that undergoes a phase change from liquid to gas, and optionally back. Such a cooling loop may comprise a tubular line having a lumen through which the refrigerant may be transported, for instance may be pumped. A hollow wall of the cooling loop may be made of a material which properly thermally isolates the refrigerant during circulation along the cooling loop. As an alternative to nitrous oxide, it is also possible to use other cooling agents, for instance liquid nitrogen, liquid helium, liquid oxygen, liquid air, argon, or the like.

An ablation source interface may be provided at the handle and may be adapted for being connected to an ablation source. Such an ablation source may be a container storing a cooling agent such as $N_2O$ or may be an electrical current source applying a heating current to the ablation catheter. The ablation source interface may be adapted for coupling or connecting to such an ablation source. The positioning control handle part may be arranged between the ablation source interface and the ablation control handle part. Thus, the propagation path of an ablation agent may be from the ablation source through the ablation source interface through the positioning control handle part subsequently through the ablation control handle part and from there into the ablation catheter for application to the surrounding tissue. In such a configuration, an ablation source line may be guided through the positioning control handle part.

An ablation source guide (such as a cooling fluid conduit or an insulated electric wire) may be provided and adapted for being connected to the ablation source via the ablation source interface and may be adapted for guiding an ablation medium (such as a cooling fluid or an electric current) from the ablation source through the positioning control handle part and the ablation control handle part towards the ablation catheter couplable to the ablation control handle part.

The ablation control handle part may be arranged at a distal position of the positioning control handle part. Thus, the ablation control handle part may be arranged between the positioning control handle part on the one hand and the positioning catheter and the ablation catheter (and thus the object in which these catheters are to be inserted) on the other hand. In other words, the ablation control handle part may be arranged closer to the ablation catheter and to the positioning catheter than the position control handle part, and therefore, in a normal operation mode, closer to the patient than the positioning control handle part. This may allow to first operate both handle parts together for a positioning procedure, and to move subsequently, for instance rotate, the ablation control handle part relative to the positioning control handle part for changing the shape of the ablation element, for instance from an essentially linear to an essentially circular configuration.

To support the turning or rotating motion for such a geometry change, specific functional measures may be taken at the handle. For example, the handle may comprise curved (for instance helical) guide elements (for instance at a connection between the positioning control handle part and the ablation control handle part, or provided at least partially in an intermediate piece sandwiched between the positioning control handle part and the ablation control handle part) to thereby allow to turn/rotate the ablation control handle part relative to the positioning control handle part to promote a shape change of the ablation catheter couplable to the ablation control handle part. Therefore, by moving the two separate handle parts relative to one another, the folding motion of the ablation element may be supported or promoted.

In an embodiment, the positioning control handle part and the ablation control handle part may be arranged to be slidable (particularly along a common longitudinal axis) with respect to one another for transforming the system between a retracted state (in which the positioning control handle part and the ablation control handle part may be close to one another, for instance may directly contact or abut to one another) and an extended state (in which the positioning control handle part and the ablation control handle part may be spaced with regard to one another so that a length of the system formed by the positioning control handle part and the ablation control handle part is larger than a corresponding length in the retracted state). In the retracted state, one of the positioning control handle part and the ablation control handle part may be at least partially accommodated in the other one of the ablation control handle part and the positioning control handle part. In such an embodiment, the positioning control handle part and the ablation control handle part may be prevented from being disassembled into two individual parts and/or may be prevented from being twisted relative to one another.

The ablation control handle part may comprise a perceivable coding feature varying along its surface indicative of a present rotational state of the handle. Hence, a physician operating the handle may easily recognize orientation of the handle for instance optically and/or haptically. This may give the physician an intuitive impression regarding an operation state such as a turning of the ablation control handle part relative to the position control handle part.

The perceivable coding feature may be a shape coding. For example, an external cross-sectional shape of the ablation control handle part may be triangular. Turning the handle by 180° may correspond with a transition of an upper surface of the ablation control handle part from a planar surface to an acute surface, or vice versa.

Additionally or alternatively, the perceivable coding feature may be a color coding. For example, different surface portions of the ablation control handle part may be provided with different colors. Turning the handle by a certain angle may correspond with a transition of a color of an upper surface of the ablation control handle part.

Additionally or alternatively, the perceivable coding feature may be a surface property coding. For instance, different surface roughness, surface markers, patterns of recesses or protrusions may provide a user with information regarding a present orientation of the handle.

Next, further exemplary embodiments of the ablation device will be explained. However, these embodiments also apply to the handle and the method.

The two catheter handle parts may be constructed in such a way that the operator may separate them by an essentially translational relative shift. Guiding elements may ensure that the inner portion of each handle may rotate in a desired fashion.

One or both of the two catheter handle parts may be supported with a turnable actuating element such as a knob or a wheel which may be actuated by a user to trigger the separation or relative movement of the two catheter handle parts.

The positioning catheter may comprise an anchoring mechanism, particularly an inflatable balloon or a biased spring (such as a helical coil), adapted for anchoring the positioning catheter at a defined position in the object. For example at a tip of the positioning catheter inserted into the human being, such an anchoring mechanism may be provided which can be operated in a passive mode in which it has a small dimension for insertion, and which can be brought to an active mode in which it has a larger dimension for anchoring. For example, when the tip of the positioning catheter is provided at a target position in the object, the anchoring mechanism may be activated, for instance an inflatable balloon may be inflated or a compressed helical coil may be expanded, so that the tip of the positioning catheter is fixed within the object. Such an actuation of the anchoring mechanism may be triggered by a physician using the handle, particularly using the positioning control part, for example by operating a button arranged there.

Moreover, the positioning catheter may comprise a guiding shaft for guiding the positioning catheter to a defined position in the object. Such a guiding shaft may be flexible and at the same time may have some mechanical stability or rigidity so that the guiding shaft can be guided through the tissue of the object to a specific position, thereby flexibly following the anatomical conditions and at the same time providing mechanical stability for proper positioning and insertion.

The positioning catheter may comprise a supply line for supplying the object with a supply medium. For instance, it may be necessary or desirable to insert a contrast agent into a specific organ or tissue of the human being so as to perform a contrast agent based measurement to ensure proper positioning of the system. Additionally or alternatively, it may be desired to insert a flushing fluid to the object, for instance a sodium chloride solution.

The ablation catheter may also comprise an ablation element adapted for ablating a defined portion of the object upon supply of an ablation medium to the ablation element by an ablation source. Such an ablation element may comprise electrodes to which an electric current can be applied for heating the tissue to destroy it. Alternatively, the ablation element may comprise a cooling tip of a cooling catheter which can be cooled by an essentially isenthalpic expansion of a cooling agent such as nitrous oxide ($N_2O$). Alternatively, the ablation element can also be an ultrasound emitter for emitting intense ultrasound to a desired position of the object, to selectively destroy tissue in a spatially selective manner.

The ablation medium may comprise a cooling medium (for example a cooling fluid such as $N_2O$, liquid nitrogen, liquid helium, etc.), a heating medium (for instance an ohmic heating element which can be heated by guiding electric current through it), a high-frequency alternating current (an oscillating current which may also heat by ohmic dissipation), an icing medium (which may cause icing of the desired tissue), ultrasound (which may also provide a high amount of energy at a specific portion of the tissue destroying the tissue), electromagnetic radiation (for example light, UV, infrared, X-rays, microwaves, etc.), laser radiation (requiring a laser source for providing laser radiation), etc. Thus, any ablation medium may be supplied to a specific portion of the tissue to destroy it.

The ablation element may comprise a shape memory material in which a predefined shape is stored. The ablation element may comprise or may consist of a shape memory material. With a shape memory material, the ablation element may be maintained in a first state and, only when mechanical pressure is applied via the handle, the material goes back to its stored shape, for instance circular shape. It is also possible that a temperature raise initiated by the body temperature upon insertion of the catheter in a physiological body triggers the ablation element to assume its original shape automatically. For instance, the shape memory material may take a predefined shape when being inserted into a warm body.

The ablation catheter may comprise a folding mechanism adapted for being actuable via the ablation control handle part to fold the ablation element into a defined folded configuration. For example, the ablation catheter may have an essentially straight configuration for an easy insertion of the catheters into the object. To bring the ablation catheter into an ablation configuration for ablating a specific portion of the tissue within the object, the folding mechanism may be actuated. The folding mechanism may be a mechanical mechanism which can be activated by exerting a mechanical force (for instance provided by the physician operating the handle) acting on the folding mechanism. For example, such a force may be enhanced by a relative motion between the two handle parts, by another pressing motion or even by a pulling force which can be actuated by moving the two handle parts relative to one another.

The ablation element may be convertible between a straight configuration and a folded configuration by actuating the ablation control handle part. The straight configuration may be appropriate for inserting the system into the object, and the folded configuration may be adjusted in accordance with the specific anatomical condition and may define a portion of the tissue which will be ablated subsequently.

The folded configuration of the ablation element may follow one of the group consisting of a loop shape, a curved line shape, an anatomical isthmus shape, and a circular shape. The folded configuration of the ablation element may follow an anatomical isthmus shape. By taking this measure, atrial flutter may be eliminated by blocking conduction in a line along the isthmus between the tricuspid valve and the inferior caval vein. Alternatively, the ablation element may follow an essentially circular shape (which may have the geometry of a loop). In such a manner (see EP 1,356,779 B1) atrial fibrillation may be eliminated in a heart of a human being.

The positioning catheter may be arranged to be at least partially guidable through the ablation control handle part. Particularly for positioning, the positioning catheter may move within the ablation control handle part.

The ablation device may comprise a (single or common or shared) shaft (which may also be denoted as a sleeve) connected to the handle and accommodating a part of the positioning catheter and a part of the ablation catheter. The shaft may be sandwiched between the handle and the portions of the ablation catheter/position catheter which are exposed to/in the object. Such a common shaft accommodating both catheter portions may be highly appropriate since it eases the insertion of the components into the body.

The shaft may have a first lumen in which the part of the positioning catheter is accommodated. Such a first lumen may have an essentially circular cross-section. Through this circular cross-section the elements related to the positioning catheter may be guided, such as a guide wire, a sodium chloride solution or any other rinse solution, contrast agent, etc. A second lumen may be provided in the shaft in which a part of the ablation catheter is accommodated. This second lumen may have a kidney shaped cross section (see FIG. 9) or may have an annulus segment shaped cross section (see FIG. 10). Supply lines and waste lines transporting the ablation medium may be arranged in this kidney or annulus segment shaped cross section. The first lumen may have a circular cross section and the second lumen may have one of a kidney shaped cross section and an annulus segment shaped cross section.

In addition to the first and the second lumen, it is possible to provide at least one further lumen in the shaft, for example to accommodate thermo couples, temperature sensors, etc.

According to an exemplary embodiment, a two-part handle for a cryocatheter may be provided, wherein a first handle portion serves for actuating a positioning catheter, and a second handle part serves for actuating an ablation catheter.

Particularly, a double lumen (or twin lumen) catheter may be provided as a shaft having a positioning catheter (which may comprise a balloon, a contrast agent supply, measurement electrodes for controlling a correct position). Furthermore, an ablation applicator may be provided (which may carry an element which is actually used for ablation, which may have a shape memory material, a thermoelectric element, and may have a cooling means supply).

For operating such a configuration, the catheters may be inserted into a body in an elongated shape. It is possible that the positioning catheter head is bendable or curvable during insertion. Subsequently, it is possible to anchor a tip of the positioning catheter in a specific portion of a heart by inflating a balloon or the like. From a backside position of the handle, it is possible to then push or provide a pushing force to thereby trigger winding of the ablation catheter, for instance to form an ablation loop or a predefined (straight or curved) ablation line. Then, a specific portion of the tissue may be destroyed by performing an ablation (in accordance with anatomical or functional requirements).

According to an exemplary embodiment, the proximal sleeve of the ablation catheter and of the positioning catheter may be provided in common forming a common shaft of the catheters. This feature may be combined advantageously with a two-part handle allowing for a separate operation of the ablation catheter and the positioning catheter.

Using a common shaft may have the advantage that it is possible to omit a taut wire (which however, in other embodiments, can be provided). The ablation catheter may be folded by pushing it from a backward position.

By providing two handles, one handle may be provided which is coupled or connected to the positioning catheter for shifting or sliding or moving the positioning catheter. Another handle portion may be connected to the ablation catheter, to initiate folding and for triggering the ablation procedure.

For inserting the apparatus into a patient, both handle portions may be connected and may be operated in common. For winding the ablation element to a circular or curved line, the two handle portions may be disconnected (so that with one hand, the positioning handle is held, and with the other hand the ablation handle is held). Then, the ablation handle may be translated/slid or rotated with regard to the positioning handle. Optionally, a loop-like guide may be defined within the two handle parts so that a helical shifting of the ablation handle may be performed which may promote a drilling of the cooling loop.

In one exemplary embodiment, the fixing mechanism at the distal end of a positioning catheter is provided by a "cryotip". Here a mechanical contact between the distal portion of the positioning catheter and the tissue serving as the anchor is established by ice-formation upon rapid cooling of the tip of a positioning catheter. Here no lethal effect is desired upon freezing. Thus, the target temperature in the tissue will typically be below 0° C. but above −30° C. In this case the positioning handle part will be connected with a refrigerant supply. In the case that extreme cold is used as an ablation medium also the ablation handle part is connected to a refrigerant supply. Different types of refrigerants may be used as different target temperatures may be desired for cryo-anchoring and cryo-ablation.

In one exemplary embodiment of the invention the anchoring portion of the positioning catheter is made from a thermally conductive material for instance a metal. In yet another embodiment a metallic anchoring area is covered by a thin layer of a material with a lower thermal conductivity (for instance 0.05 mm to 0.5 mm of a plastic). This layer defines a desired thermal resistance which ensures that the tissue temperature does not drop below −30° C. even if the temperature in the boiling chamber inside the anchoring area is far below −30° C. (for instance about −90° C. when using nitrous oxide as a refrigerant).

In yet another embodiment thermoelectric cooling (for instance a Peltier element) is applied for creating the desired temperatures below 0° C. but above −30° C. for anchoring the positioning catheter. A Peltier element may be a heat pump realized by properly connected and donated semiconductors (and/or realized by metals) with transports heat from a cold region to a warmer region when current is delivered. Here the positioning catheter contains at least two thermally conducting regions. One cold anchoring region which freezes to the tissue and one warmer region (warmer than the body temperature) where the heat flow of the thermoelectric cooler is dissipated to the blood flow. Here, the surface of the warm side is large enough to dissipate the by temperatures less than 10° C. above body temperature. Thus, the warm area does not harm the tissue.

In yet another embodiment the anchoring portion of the catheter is formed only by an essentially cylindrical structure of proper diameter (typically between 1 mm and 3 mm) and a proper length (typically between 10 mm and 25 mm). Such a structure may be sufficient for positioning a catheter within a vessel branching from the heart (for instance a pulmonary vein). The structure should be long enough to guide the distal axis of the positioning catheter in the direction of the vessel.

In the following, further aspects are disclosed:

Aspect 1: A positioning device for positioning a medical apparatus in an object, the positioning device comprising
a coolable element which is adapted to be fixed to the object by freezing the coolable element to the object.

Aspect 2: The positioning device according to aspect 1, comprising a control unit adapted for controlling the coolable element to be cooled to a cooling condition which is non-lethal for the object, particularly for human tissue.

Aspect 3: The positioning device according to aspect 2, wherein the control unit is adapted for controlling the coolable element to be cooled to temperatures which are prevented from falling below −30° C.

Aspect 4: A medical apparatus, the medical apparatus comprising
a positioning device according to any one of aspects 1 to 3;
a surgical device adapted for performing a surgical treatment of the object and cooperating with the position device.

Aspect 5: The medical apparatus of aspect 4, wherein the surgical device comprises an ablation device as mentioned above.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

The illustration in the drawing is schematically. In different drawings, similar or identical elements are provided with the same reference signs.

FIG. 1 shows a handle 100 for an ablation device (see FIG. 2 to FIG. 4, FIG. 7, FIG. 8) according to an exemplary embodiment of the invention.

Figure 1:
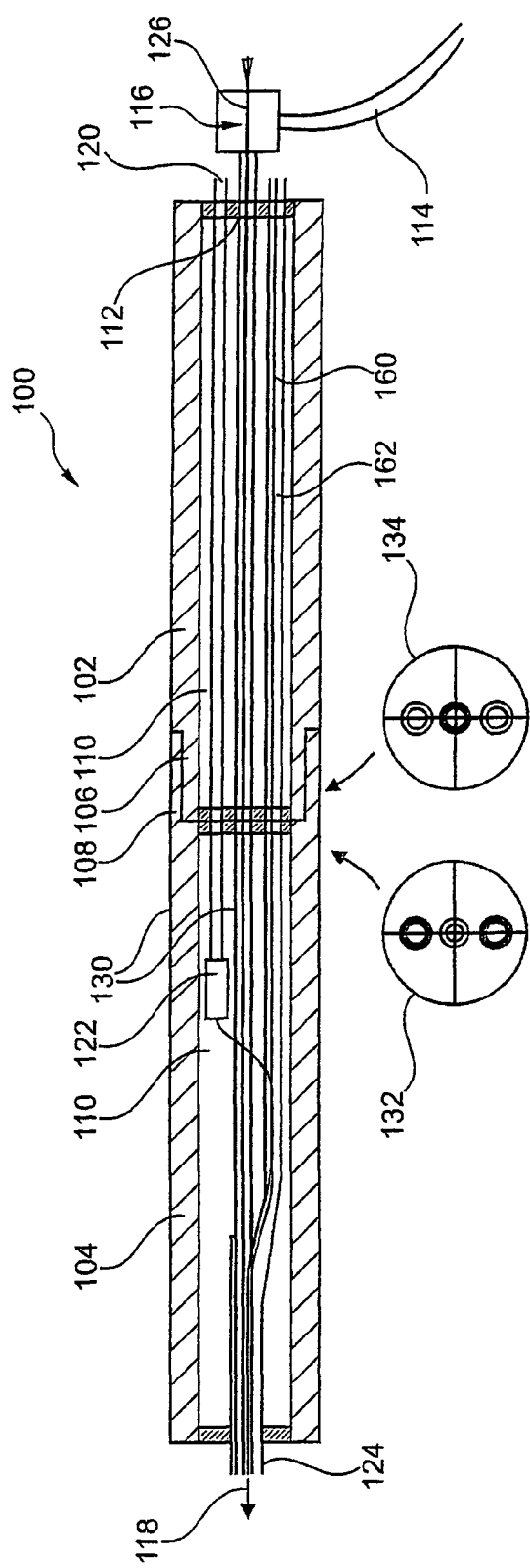
FIG. 1 illustrates a handle according to an exemplary embodiment.

The handle 100 comprises a positioning control handle part 102 adapted to be coupled to a positioning catheter of the ablation device and adapted to position the positioning catheter in a patient. Furthermore, the handle 100 comprises an ablation control handle part 104 adapted to be coupled to an ablation catheter of the ablation device and adapted to ablate material of the patient using the ablation catheter. By plugging a male part 106 of the positioning control handle part 102 into a female recess 108 of the ablation control handle part 104, it is possible to selectively connect the positioning control handle part 102 to the ablation control handle part 104 or to separate both control handle parts 102, 104 from one another.

In a connected operation mode of the components 102, 104 (as shown in FIG. 1), the positioning control handle part 102 and the ablation control handle part 104 are rigidly connected to one another. In this operation mode, they can be used to insert a positioning catheter into a human body. In a second operation mode, the positioning control handle part 102 may be separated or disassembled from the ablation control handle part 104 so that the ablation control handle part 104 can be moved alone towards the object (for instance to trigger a winding of the ablation catheter) while the positioning control handle part 102 is maintained essentially spatially fixed.

As can be taken from FIG. 1, the positioning control handle part 102 and the ablation control handle part 104 form a common lumen 110 through which a plurality of items are guided. A cooling medium supply line 160 is connected at the positioning control handle part 102 so as to allow connecting a nitrous oxide source as a cooling agent via a supply line 160 to guide it towards the ablation catheter (see arrow 118). Furthermore, a cable 120 is guided through the lumen 110. The cable 120 is connected to an electronic module 122 (which may be an integrated circuit) which may provide an electronic function.

A common sleeve or shaft 124 accommodates all components needed for a communication of fluids and electric signals between the handle 100 and the catheters of the cryoablation device (not shown).

A guiding wire is denoted with reference numeral 126 and is guided through the lumen 110 towards the catheters. At the interface 106, 108, a plurality of sealing units 130 (such as sealing rings) are provided.

Furthermore, cross sections 132, 134 show the various connections formed around the sealing portion 130.

A bank of taps (not shown) may be provided coupled to the cooling line 160.

The handle 100 may be arranged as a two-part handle 102, 104 for twin catheters. The handle portion 102 is assigned to the positioning catheter, and the other handle portion 104 (ablation handle) is assigned to the ablation catheter. All components related to the ablation catheter (supply of the ablation energy, electronics) are fixedly connected or connected via plug connections. All supply connections related to the positioning catheter (for instance contrast agent, flushing solution or rinse fluid) are connected to the positioning handle 102. The ablation handle 104 is arranged at a distal position from the positioning handle 102 and is detachably connected to it (for instance by a plug connection, a bayonet connection). The positioning catheter is slidable via the ablation handle 104. The connected handles 102, 104 define the passive position for inserting and positioning, and for retracting the catheters. For bringing the catheter into an active position (for ablation), the ablation handle 104 is slid in a direction distally from the positioning handle 102, so that the ablation catheter slides over the positioning catheter.

As an alternative to FIG. 1, the positions of the handles 102, 104 can be exchanged.

A flushing line 114 is connected to the haemostatic valve 116.

A cooling fluid drain (refrigerant backflow) unit for guiding the expanded cooling fluid apart or away from the device 100 is denoted with reference numeral 162.

Figure 3:
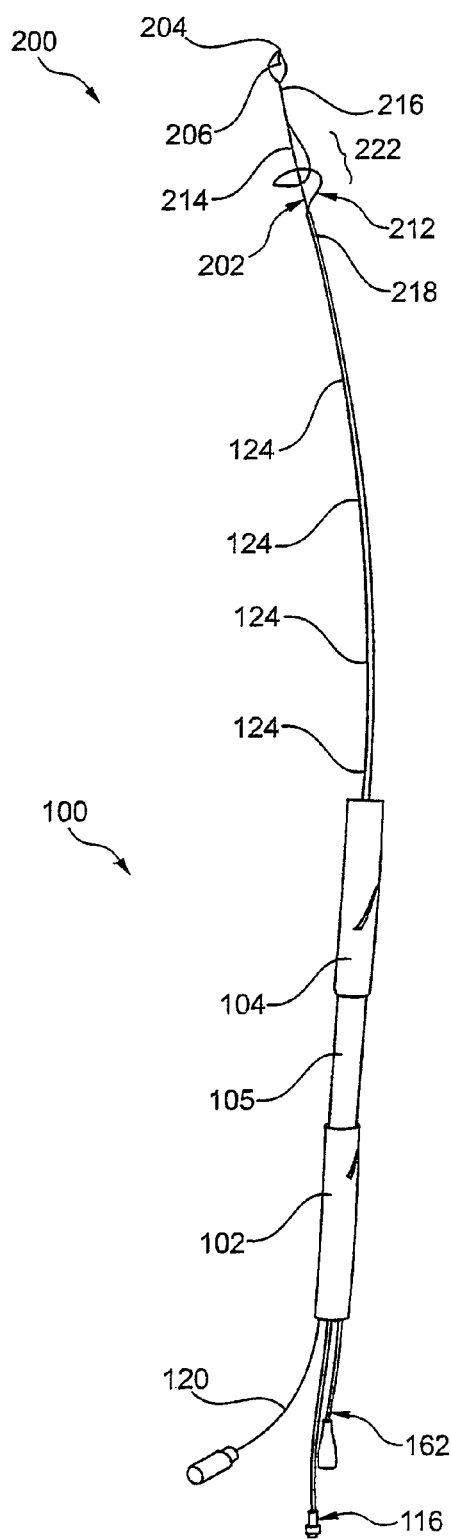
FIG. 3 shows the cryoablation device of FIG. 2 in a laterally expanded operation mode.
Figure 2:
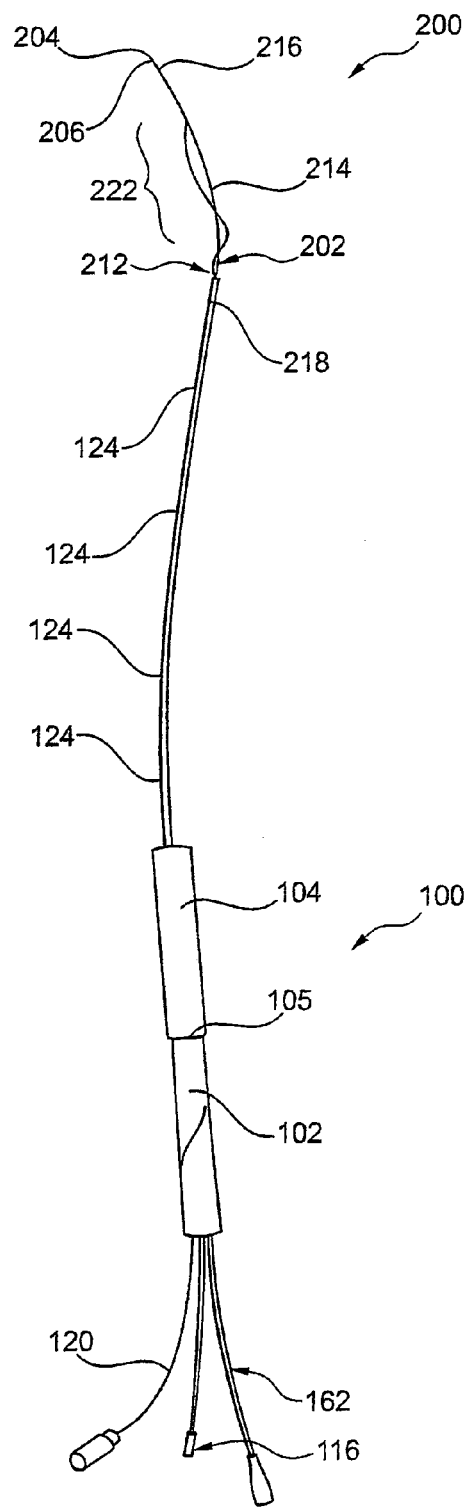
FIG. 2 illustrates a cryoablation device according to an exemplary embodiment in an elongated operation mode.

FIG. 2 and FIG. 3 show a cryoablation device 200 inserted into human heart tissue according to an exemplary embodiment of the invention in different operation modes.

As can be taken from FIG. 2 and FIG. 3, a handle 100 as shown in FIG. 1 may be connected to a proximal end portion of the cryoablation device 200.

As becomes clear from FIG. 2, the ablation device 200 incorporates a positioning catheter 202 (which may or may not be steerable), which has in front of its distal end 204 a inflatable balloon 206. In FIG. 3, the balloon 206 is shown in its inflated condition in which it fixes the distal end 204 of the catheter 202 in an orifice opening (not shown) of a pulmonary vein in the atrium of the heart. The positioning catheter 202 may be provided with a lumen for a guide wire, a deflection device for the targeted guiding of the distal end 204, etc.

An ablation catheter 212 is disposed on a shank 214 of the positioning catheter 202. For displaceable guidance of the ablation catheter 212 on the positioning catheter 202, provision is made for two guide sleeves 216, 218, which are formed on the distal end 204 or at a distance therefrom by some centimeters in the proximal direction, and which may be shifted along the positioning catheter 202.

In the area between the two guide sleeves 216, 218, the ablation catheter 212 is provided with an ablation applicator 222 in the form of a thermally conducting tube for cryoablation.

FIG. 2 shows the straight position of the ablation applicator 222, from which it can be taken to the radially expanded ablation position shown in FIG. 3 by separating the ablation handle part 104 from the catheter handle part 102. An intermediate piece 105 defines a common axis and the maximal displacement. By shifting the ablation catheter 212 in a rotating fashion towards the distal end the ablation applicator 222 is brought into a circular-arc-type encircling configuration based on an appropriate pre-shaping of the ablation catheter 212. The ablation applicator 222, in the process, covers an angle at circumference P of more than 180° so that the ablation applicator 222, in this ablation position, extends over more than half of the circumference of the circular lesion to be formed.

The formation of the circular lesion shall briefly be illustrated below, with the aid of FIG. 2 and FIG. 3. The positioning catheter 202, accordingly, is entered with a non-dilated balloon 204 as shown in FIG. 2 via a transseptal puncture into the left atrium of the heart where the orifices of all pulmonary veins are mapped by conventional means. After confirming the correct position of the distal end 204 of the positioning catheter 202 inside the orifice opening of the desired pulmonary vein, the balloon 206 is dilated and the positioning catheter 202 is thus fixed in the orifice opening.

Then the ablation catheter 212 is advanced along the shank 214 of the positioning catheter 202 as far as into the position, seen in FIG. 2, in front of the distal end 204 of the positioning catheter 202. The ablation applicator 222 is positioned proximally before the balloon 206 in the vicinity of the atrium in front of the orifice opening. By simultaneous translational displacement and rotation around the longitudinal axis of the ablation catheter 212 relative to the positioning catheter 202, the proximal guide sleeve 216 is pushed ahead and the ablation applicator 222 is moved into the ablation position, in which the thermally conducting portion, covers the angle at circumference P, rest on the endocardium in the atrium. By delivery of a refrigerant, part of the circular lesion is obtained. As the case may be, the ablation applicator 222 is then partially moved into the passive position seen in FIG. 2, rotated by 180° and again expanded in the way of a circular arc into the ablation position seen in FIG. 3. Retracting, rotating and again advancing the applicator 222 is also possible in the bent condition. Thus, the ablation applicator 222 fits tightly on an area of the endocardium of the atrium where a lesion has not previously been applied. By renewed emittance of refrigerant, the circular lesion around the orifice opening is completed.

The average size of the left atrium of a heart is approximately 40 mm; however, it is significantly larger in patients with chronic atrial fibrillation, amounting to 60 mm and more; therefore the effective diameter of the ablation applicator 222, in the ablation position 208, should range from 5 to 25 mm for small blood vessels (for instance the inferior pulmonary vein). In the case of enlarged atrial or pulmonary veins, effective diameters are in the range of 25 to 60 mm.

The ablation applicator 222 may assume a loop shape when being slid in a forward direction, due to the memory shape. The loop formation can be supported by a simultaneous turning of the ablation handle 104. In an embodiment, this turning motion can be promoted by helical guide elements at the contact position of the two handle elements.

Figure 4:
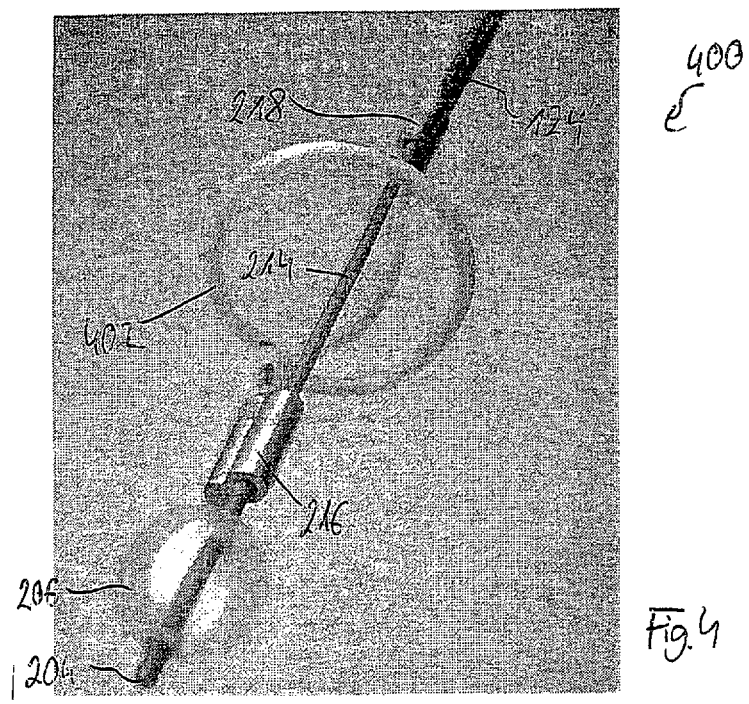
FIG. 4 is an image of an ablation device according to an exemplary embodiment.

FIG. 4 shows an image 400 of a cryoablation catheter 400 according to an exemplary embodiment of the invention.

In contrast to the device 200 as shown in FIG. 2 and FIG. 3, the ablation device 400 comprises a cryoablation catheter 402 through which an extremely cold gas or liquid may be guided for ablating surrounding tissue by icing.

Figure 5:
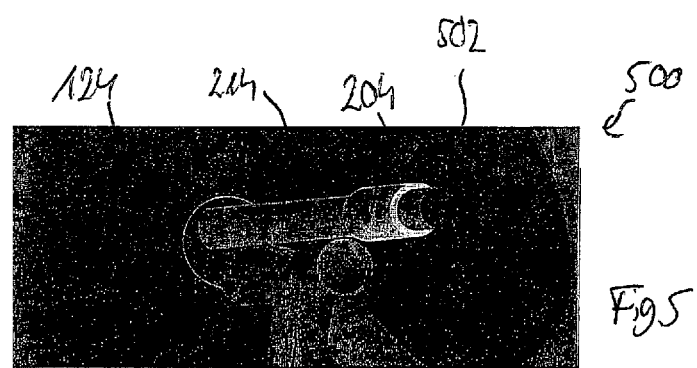
FIG. 5 shows a common shaft for an ablation catheter and a positioning catheter according to an exemplary embodiment.

FIG. 5 shows an arrangement 500 showing details regarding the geometry of the common shaft 124 with respect to the other components.

Figure 6:
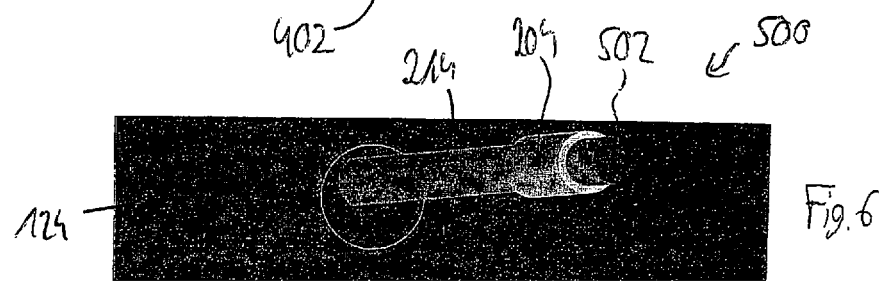
FIG. 6 shows the shaft of FIG. 5. The ablation applicator has been removed in order to make the two lumen of the shaft visible.

In FIG. 6, the same configuration is shown without the cool loop 402, for a simplified view of the other components.

As can be taken from FIG. 5 and FIG. 6, the shaft 214 comprises an inner lumen 502 through which a contrast agent or the like may be supplied.

Figure 7:
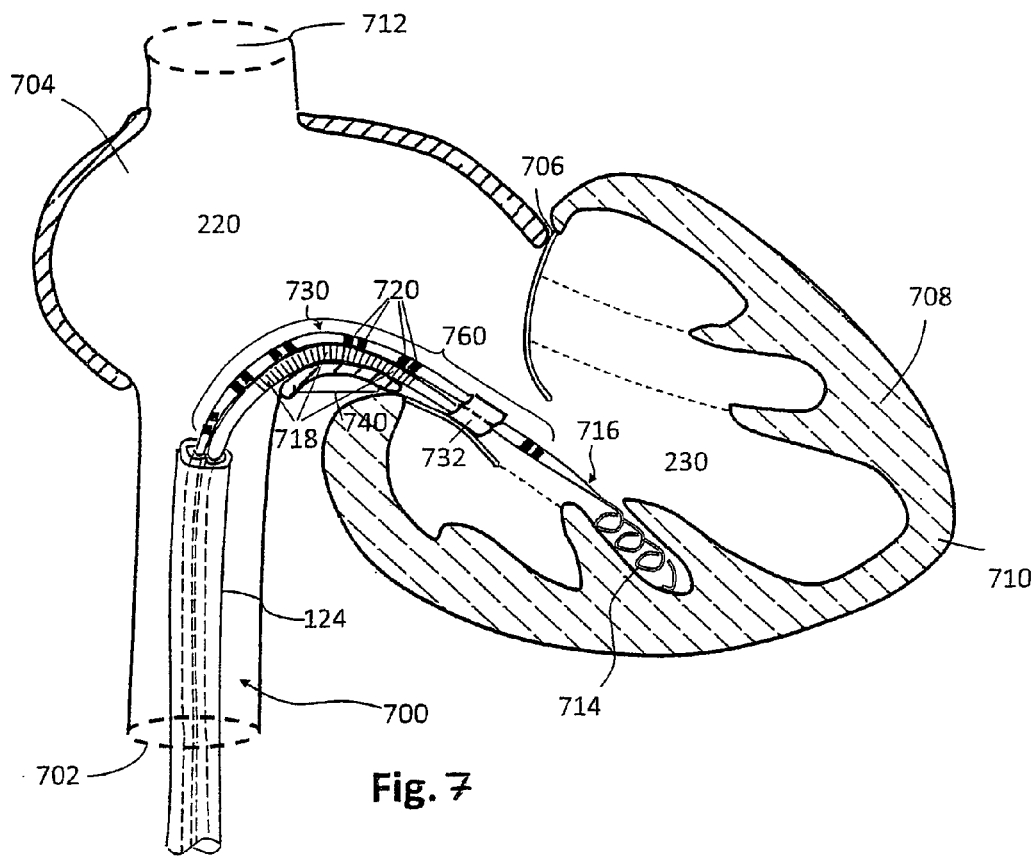
FIG. 7 shows an ablation device according to an exemplary embodiment inserted into a human heart.

FIG. 7 shows an ablation device 700 according to an exemplary embodiment of the invention which is inserted into a human heart.

The inferior vena cava is denoted with reference numeral 702. The right atrium is denoted with reference numeral 704. The tricuspid annulus is denoted with reference numeral 706. Reference numeral 708 shows the right ventricle. Reference numeral 710 shows the apex, reference numeral 712 shows the superior vena cava.

A helical winding 714 is provided at an end of the ablation device 700 so that the helical winding 714 can serve as an anchoring mechanism for connecting the tip of a positioning catheter 716 in a specific portion of the heart, for instance the right ventricle. An ablation applicator 718 is positioned in such a manner that the isthmus tissue 740 can be deactivated by cooling the ablation applicator 718. Ring electrodes 720 are provided for performing a measurement of the position of the positioning catheter 716, so that the correct positioning of the ablation device 700 in the heart can be ensured. After a proper positioning of the positioning catheter 716 and the ablation catheter 730 guided through the common shaft 124, the ablation procedure may be started by delivering cooling agent through the ablation applicator 718.

According to the embodiment of FIG. 7, the ablation catheter 730 may be provided for the interventional therapy of isthmus dependent atrial flutter. The isthmus 740 is a small muscle bridge between the intersection of the inferior vena cava 702 and the tricuspid annulus 706. In patients having isthmus dependent atrial flutter, the isthmus 740 has a conductivity for the electrical activation pulse and therefore forms the substrate of the re-entrant arrhythmia. An interruption of this line by an ablation is supposed to eliminate the arrhythmia.

The ablation device 700 shown in FIG. 7 has a double lumen design (twin catheter). The two catheter portions are the positioning catheter 716 and the ablation catheter 730. The positioning catheter 716 comprises at its distal end the anchoring helical coil 714. By suitable control mechanisms, the positioning catheter 716 is advanced into the right ventricle 708. For this purpose, a taut wire, a sluice, a guiding wire, etc. may be used. By means of the anchorable helical coil 714, the positioning catheter 716 is anchored at its tip in the right ventricle 708.

Proximal from the helical coil 714, the ring electrodes 720 are arranged along a certain extension (catheter neck 760). In an embodiment, the ring electrodes 720 are arranged in a pairwise manner so that for example bipolar electrograms can be measured. By a moderate pull at the proximal catheter end (handle), a portion of the catheter neck 760 abuts against the isthmus 740. By an evaluation of the electrograms it can be determined in which position the catheter device 700 is abutting at the isthmus (ablation target) 740.

The ablation catheter 730 can be guided via sleeves s 732 at the positioning catheter 716. At the distal end, the ablation applicator 718 is provided which can be slid in a forward or backward direction (see sleeve 732). This can be performed using a sliding carriage mechanism.

The ablation applicator 718 can also be positioned under the assistance of imaging methods (for instance X-ray imaging) wherein the electrodes 720 may serve as markers of the isthmus 740. By the distal fixing of the positioning catheter 716, it is now possible by forceful pulling at the twin catheter to smoothly press the isthmus 740 to the contact line 718 of the catheter 730, in order to provide a proper contact.

The carriage of the ablation applicator 718 may be slid in a forward direction and can be positioned via marking electrodes 720 at the isthmus 740.

Figure 8:
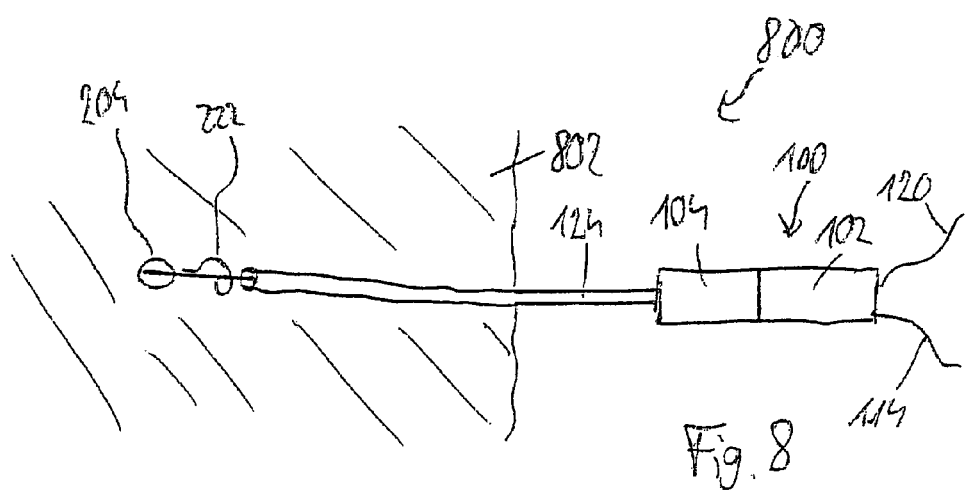
FIG. 8 shows an ablation device according to another exemplary embodiment.

FIG. 8 shows another schematic embodiment of the invention, illustrating an ablation device 800. The ablation device 800 is inserted into human tissue 802. FIG. 8 shows the entire system 800 and how the different components are arranged with respect to one another.

Figure 9:
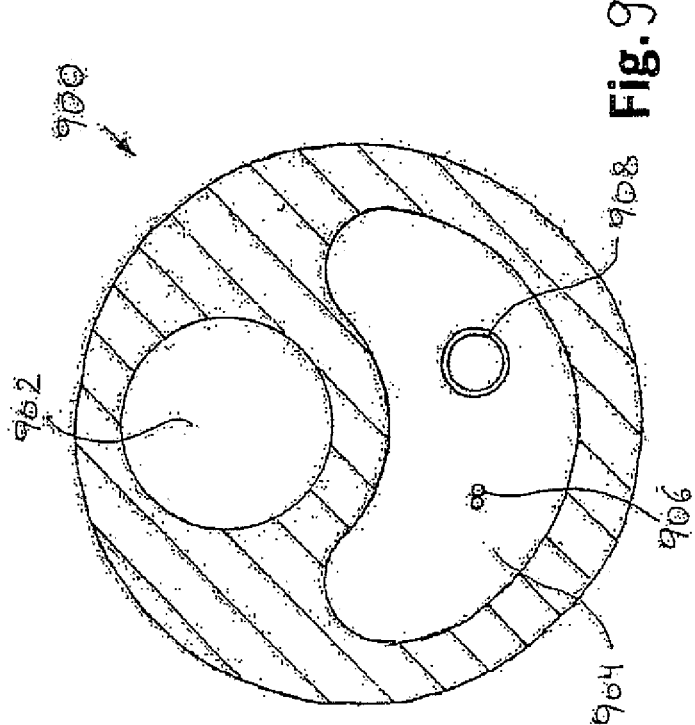

FIG. 9 shows a cross section of a common shaft 900 according to an exemplary embodiment.

The common shaft 900 for receiving components of the positioning catheter and the ablation catheter comprises a circular lumen 902 through which the components for operating the positioning catheter can be guided. For instance this lumen is flushed by a sodium chloride solution. Through a kidney shaped lumen 904, various components for the ablation catheter may be guided such as a thermo element 906 for performing a temperature measurement, a cooling agent supply line 908 and a cooling agent backflow lumen 904. The material of the shaft 900 may be a plastic material or any other suitable flexible material. Via the supply line 908, a cooling agent (such as $N_2O$) can be conducted to a tip of the ablation catheter, and via the backflow lumen 904, the expanded cooling agent in gaseous form may be transported back to the exhaustion.

Figure 10:
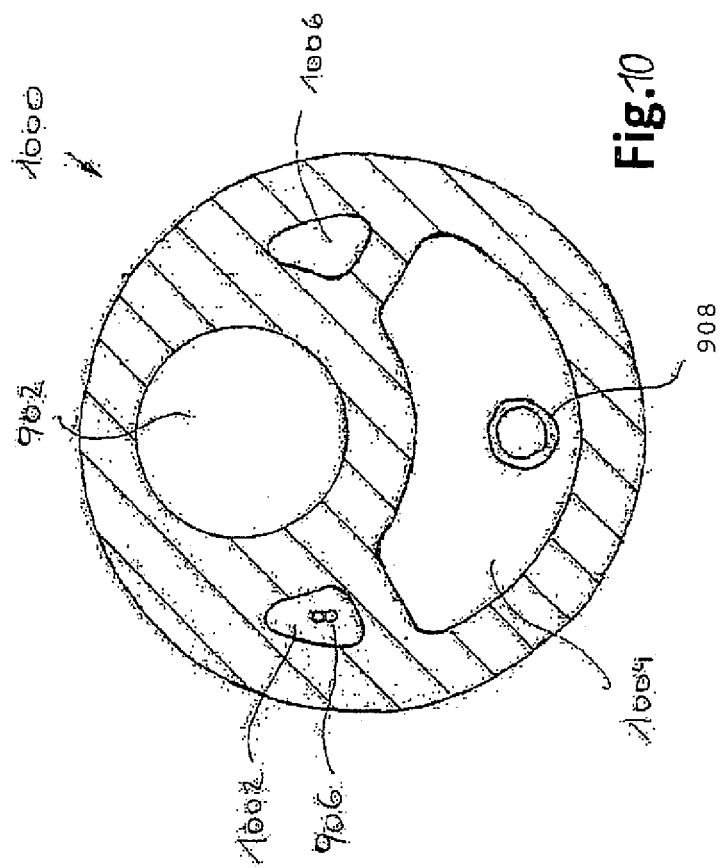
FIG. 9 and FIG. 10 show cross sections of integrally formed shafts for receiving ablation catheter and positioning catheter according to an exemplary embodiment.

FIG. 10 shows a common shaft 1000 according to another exemplary embodiment of the invention.

In the embodiment of FIG. 10, the thermo couple 906 is provided in a separate lumen 1002 so as to avoid undesired interaction with other components. An annulus segment shaped lumen 1004 is provided which accommodates a cooling agent supply line 908 and a cooling agent backflow lumen 1004. At least one further lumen 1006 may be provided to accommodate optional further elements. In an alternative embodiment one pathway, for instance the backflow of the cooling agent, may be parallel in multiple lumen, e.g. 1002, 1004 and 1006. Here, the bridges between the separated lumen of one pathway increase the stiffness of the catheter tube to prevent for kinking.

Thus, it is possible to implement a shaft 900, 1000 for use with an oblong shaft of the ablation catheter having two lumen. One lumen having a kidney shaped cross section (see reference numeral 904) and a second lumen 902. The kidney shaped lumen 904 can be used as an inner lumen of the ablation applicator. In this lumen 904, all required lines for supplying the ablation energy may be provided. The other lumen 902 having essentially circular cross section may receive components of the positioning catheter. By the circular cross section, an undesired drilling of the components relative to one another may be performed.

The material of the shaft 1000 may be stiff to be mechanically stable.

Figure 11:
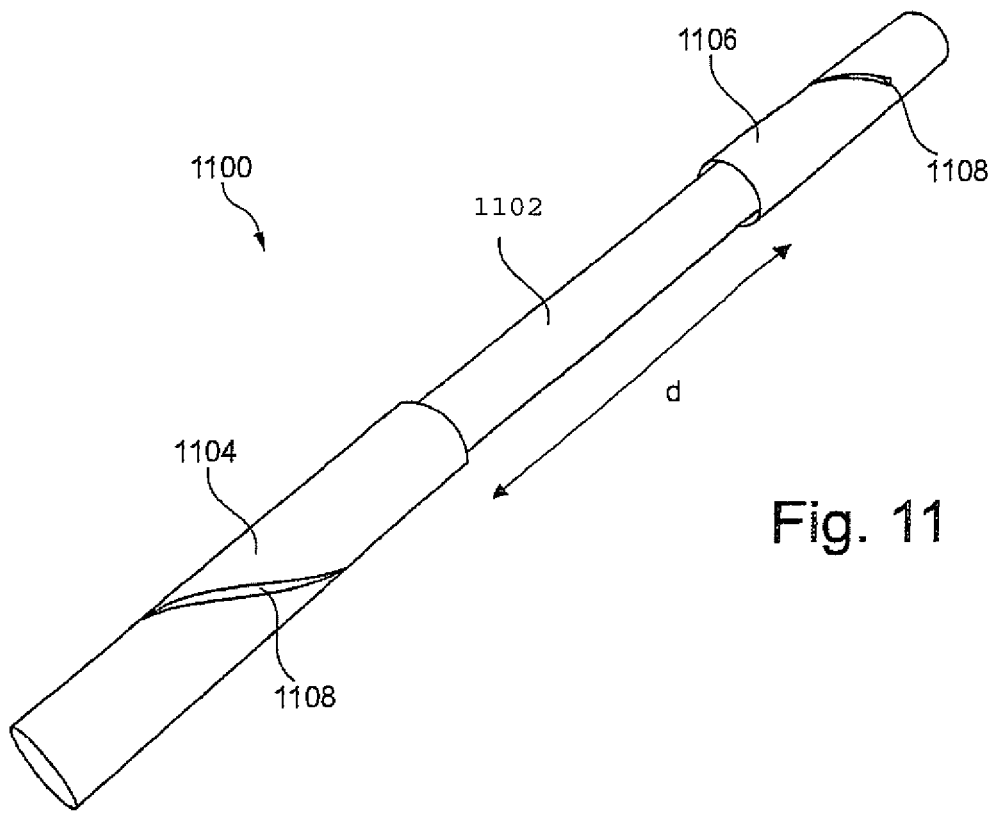
FIG. 11 illustrates a handle according to an exemplary embodiment in a first operation mode.
Figure 12:
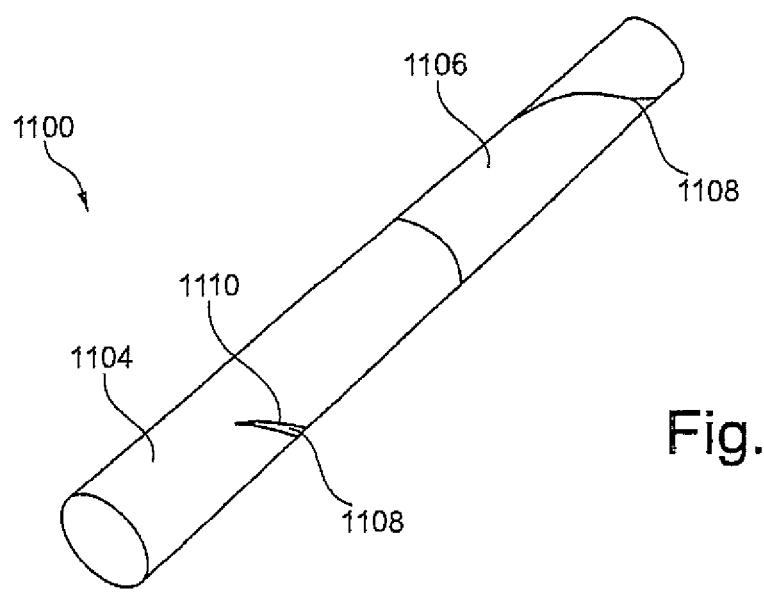
FIG. 12 illustrates the handle of FIG. 11 in a second operation mode.

FIG. 11 and FIG. 12 illustrate a handle 1100 according to an exemplary embodiment in different operation modes.

FIG. 11 shows the handle 1100 in an extended state, whereas FIG. 12 shows the handle 1100 in a retracted state.

The handle 1100 comprises a tubular intermediate piece 1102 connected between a tubular positioning control handle part 1104 and a tubular ablation control handle part 1106. The tubular intermediate piece 1102 has a slightly smaller diameter than the tubular positioning control handle part 1104 and the tubular ablation control handle part 1106. In the operation mode of FIG. 11, the tubular intermediate piece 1102 serves as a spacer for keeping the positioning control handle part 1104 at a distance d from the ablation control handle part 1106. In the operation mode of FIG. 12, the tubular intermediate piece 1102 is received/accommodated within the positioning control handle part 1104 and in the ablation control handle part 1106 so that the positioning control handle part 1104 almost abuts against the ablation control handle part 1106. The tubular intermediate piece 1102 serves to allow to either spatially separate the positioning control handle part 1104 from the ablation control handle part 1106, or to allow to have the positioning control handle part 1104 and the ablation control handle part 1106 close together.

Each of the tubular positioning control handle part 1104 and the tubular ablation control handle part 1106 comprises a helical guide groove 1108 along which a guide pin 1110 can be guided to convert the handle 1100 between the extended state and the retracted state, by a turning hand movement.

The configuration, operation and internal construction of the tubular positioning control handle part 1104 and the tubular ablation control handle part 1106 may be similar as described above, for instance referring to FIG. 1.

Figure 13:
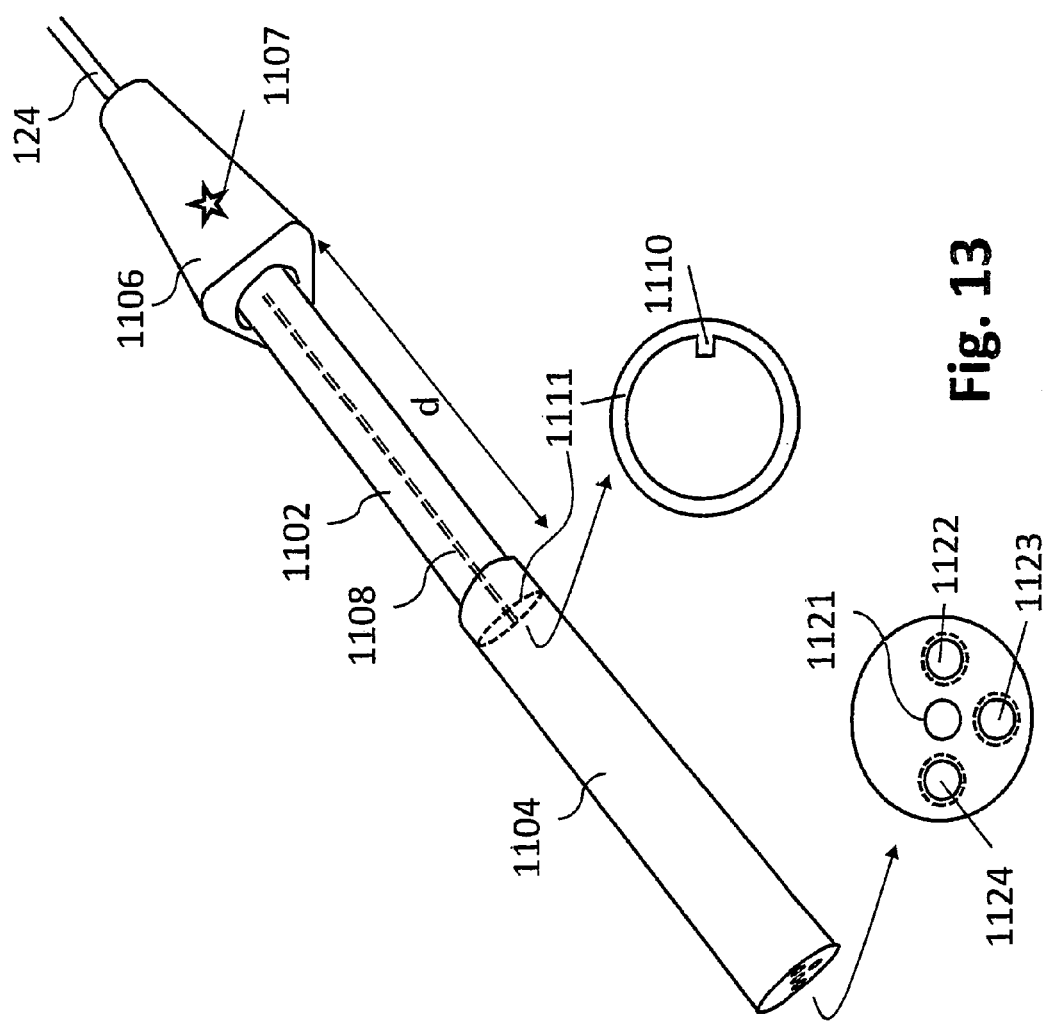
FIG. 13 illustrates another embodiment of the handle.

FIG. 13 shows another exemplary embodiment of the handle. Here the handle is designed to allow only a relative transversal shift of both handle parts 1106 and 1104 but not relative rotation. The intermediate piece 1102 is fixedly attached to the distal handle part 1106 such that no movement of these two pieces relative to another is possible. The intermediate piece 1102 contains a longitudinal groove 1108. A ring 1111 with a guide pin 1110 is fixedly attached (for instance non-detachably) within the proximal piece part 1104. The guide pin 1110 slides within the groove 1108 and ensures that the two handle parts 1104 and 1106 can be shifted only transversally along their common axis.

The proximal handle part 1106 has in a part an essentially triangular shape and may be labeled with one or a plurality of optical markers 1107. The combination of a distinct shape and optical markers enables an identical perception of angular rotation by the user when the entire device (both handle parts 1104 and 1106 together with the shaft 124) are rotated relative to a sheath (not shown) used for introducing the catheter into the venous system. Thus, when rotating the catheter around its axis within the heart the corresponding handle rotation can be easily recognized by the user. The triangular shape of the distal handle part 1106 defines also an enlarged volume within the handle which can be used for including additional components (for instance a pressure control valve in the refrigerant return path) within the handle.

As no relative rotation of the two handle parts is allowed, concentric tubes can be used for defining multiple lumina (1122, 1123, 1124) through which the concentric refrigerant supply (160 and 162), the electric cable 120 and the flushing tube 114 are slidably guided. The inner tubes in the lumina (solid circles around 1122, 1123 and 1124) are fixedly attached to the proximal handle part 1104 while the outer tubes (dashed circles around 1122, 1123 and 1124) are fixedly attached to the intermediate piece 1108. The concentric tubes slide relative to each other when the handle parts are shifted relative to each other. The central lumen 1121 is fixedly attached with the positioning catheter 202. Through this lumen the guide wire is introduced in the positioning catheter. The flushing tube is connected to the guide wire lumen within the proximal handle part for instance by a standard connector used for flushing a guide wire lumen.

In the following, some further explanations of exemplary embodiments of the invention will be given.

The complex mechanism of atrial fibrillation can be treated with a simple and effective surgery technique. Such an instrument is shown in FIG. 2 and FIG. 3. An effective separation of the left atrium into separate electrically isolated portions allows for an effective treatment of atrial fibrillation, since multiple mechanisms of atrial fibrillations may be prevented.

Using an ablation device according to an exemplary embodiment allows to generate long lesions, so that a cardiologist has an instrument which allows for the easy generation of long lesions in the left atrium. The catheter may be formed of two parts: The guide catheter with a fixing mechanism (for instance a balloon) at a distal end and an ablation applicator (for instance a cooling loop) which may be made of shape memory material. The guide catheter is first positioned in one of the lung veins using a steerable sheath, and may then be fixed by inflating a distal balloon. Then, the ablation applicator may be shifted in a forward direction through the sheath and assumes a loop shape due to the shape memory property. The loop can be pressed against the atrium wall. By inserting a cooling agent (such as $N_2O$), the tissue may be shock frozen and may therefore be destroyed over the entire length of the loop.

When this treatment is performed for all probable cardiac openings, this may result in the generation of long (for instance 10 cm) interconnected ablation lines around the lung veins to separate the left atrium. Thus, an efficient tool may be provided which allows to perform an efficiently surgical or interventional procedure ("Maze procedure") to generate compartments in the left atrium using a catheter ablation.

As compared to conventional catheter ablation, the intervention may be significantly simplified (purely anatomical treatment), and the rate of success can be increased by exemplary embodiments of the invention.

According to an exemplary embodiment of the invention, a taut wire mechanism (see reference numeral 226 in FIG. 2, FIG. 3) may be omitted.

Using an appropriate ablation medium (for instance high frequency alternating current, icing, ultrasound, laser, microwave), a destroyed line can be generated at the contact portion, for instance by cryoablation. It is possible to perform a plurality of ablation procedures to obtain a desired ablation geometry.

Further connections for rinse fluid, contrast agents, etc. are possible.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. A cryoablation device comprising:
a positioning control handle part coupled to a positioning catheter of the cryoablation device and adapted to position the positioning catheter in an object;
an ablation control handle part coupled to an ablation catheter of the cryoablation device to ablate material of the object using the ablation catheter via application of a cooling agent as an ablation medium;
an intermediate part positioned between the positioning control handle part and the ablation control handle part; and
a set of concentric tubes extending through the position control handle part, the intermediate part and the ablation control handle part including a supply lumina for slidably guiding a concentric cooling agent supply and a draining lumina larger than the supply lumina for draining exhausted cooling agent,
wherein the positioning control handle part and the ablation control handle part are operable in a first configuration in which the positioning control handle part and the ablation control handle part are operable together, and are operable in a second configuration in which the positioning control handle part and the ablation control handle part are spaced from each other and at least one of the positioning control handle part and the ablation control handle part are operable independently from each other, is spaced from and operable independently from the other one of the positioning control handle part and the ablation control handle part,
wherein in the first configuration the positioning catheter is positionable at a defined position in the object and in the second configuration a shape of the ablation catheter is adjustable by movement of the ablation control handle part relative to the positioning control handle part for changing the shape of the ablation catheter from an essentially linear to an essentially loop shaped configuration relative to a longitudinal axis of the ablation catheter and to bring the ablation catheter into contact with a portion of the object to be ablated,
wherein the ablation catheter comprises a shape memory material having a substantially loop shaped configuration as a stored shape, and
wherein the concentric tubes are fixedly attached to the positioning control handle part and the intermediate part so that the concentric tubes slide relative to each other when the positioning control handle part and the ablation control handle part are shifted relative to each other.

2. The device according to claim 1, wherein the positioning control handle part and the ablation control handle part are adapted to be fixedly connectable to one another in a detachable manner.

3. The device according to claim 1, wherein the positioning control handle part and the ablation control handle part further comprise an additional common lumen for a flushing line or electric cabling.

4. The device according to claim 1, comprising an ablation source interface adapted for being connected to an ablation source.

5. The device according to claim 4, wherein the positioning control handle part is arranged between the ablation source interface and the ablation control handle part.

6. The device according to claim 4, comprising an ablation source guide connected to the ablation source via the ablation source interface.

7. The device according to claim 1, wherein the ablation control handle part is arranged between the positioning control handle part on one side and both the positioning catheter and the ablation catheter on the another side.

8. The device according to claim 1, wherein the positioning control handle part and the ablation control handle part are arranged to be bidirectionally slidable, with respect to one another for converting the device between a retracted state and an extended state, wherein in the retracted state, the positioning control handle part is partially accommodated within the ablation control handle part.

9. The device according to claim 1, wherein the ablation control handle part comprises a perceivable coding feature along its surface indicative of a rotational state of the device.

10. The device according to claim 1, wherein at least a part of the ablation control handle part has an essentially triangular shape.

11. A cryoablation device, the cryoablation device comprising:
a handle;
a positioning catheter; and
an ablation catheter;
wherein the handle comprises a positioning control handle part coupled to the positioning catheter of the cryoablation device to position the positioning catheter in an object;

an ablation control handle part coupled to the ablation catheter of the cryoablation device to ablate material of the object using the ablation catheter via application of a cooling agent as an ablation medium;

an intermediate part positioned between the positioning control handle and the ablation control handle part;

a set of concentric tubes extending through the position control handle part, the intermediate part and the ablation control handle part including a supply lumina for slidably guiding the cooling agent and a draining lumina larger than the supply lumina for draining exhausted cooling agent, and a pressure control valve in the draining lumina to prevent over pressure in the draining lumina;

wherein the positioning control handle part and the ablation control handle part are operable in a first configuration in which the positioning control handle part and the ablation control handle part are nearly adjacent to one another and are operable in a second configuration in which at least one of the positioning control handle part and the ablation control handle part is spaced from and operable independently from the other one of the positioning control handle part and the ablation control handle part, wherein in the first configuration the positioning catheter is positionable at a defined position in the object and in the second configuration a shape of the ablation catheter is adjustable by movement of the ablation control handle part relative to the positioning control handle part for changing the shape of the ablation catheter from an essentially linear to an essentially loop shaped configuration relative to a longitudinal axis of the ablation catheter and to bring the ablation catheter into contact with a portion of the object to be ablated, and wherein the ablation catheter comprises a shape memory material having a substantially loop shaped configuration as a stored shape, and wherein the concentric tubes are fixedly attached to the positioning control handle part and the intermediate part so that the concentric tubes slide relative to each other when the positioning control handle part and the ablation control handle part are shifted relative to each other.

12. The cryoablation device according to claim 11, wherein the positioning catheter comprises at least one of:
an anchoring mechanism, being either an inflatable balloon or a biasable spring, adapted for anchoring the positioning catheter at a defined position in the object; and
a guiding shaft for guiding the cryoablation device to a defined position in the object.

13. The cryoablation device according to claim 12, wherein the anchoring mechanism is adapted for anchoring the positioning catheter at a defined position in the object by anchoring a portion of the positioning catheter in tissue of the object.

14. The cryoablation device according to claim 11, wherein the ablation catheter comprises an ablation element adapted for ablating a defined portion of the object upon supply of the ablation medium to the ablation element by an ablation source.

15. The cryoablation device according to claim 11, wherein the positioning catheter is arranged to be guidable at least partially through the ablation control handle part.

16. The cryoablation device according to claim 11, comprising a common shaft connected to the handle and accommodating a part of the positioning catheter and a part of the ablation catheter.

17. A method of operating a cryoablation device, the method comprising the steps of:
coupling a positioning control handle part to a positioning catheter of the cryoablation device;
operating the positioning control handle part to position the positioning catheter in an object;
coupling an ablation control handle part to an ablation catheter of the cryoablation device; and
operating the ablation control handle part to cryoablate material of the object using the ablation catheter by supplying liquid refrigerant at high pressure through a supply lumina in the positioning control handle part and the ablation control handle part and draining exhausted gaseous refrigerant through a draining lumina concentric with and larger than the supply lumina;

wherein the positioning control handle part and the ablation control handle part are separable from one another and further include an intermediate part positioned there-between, wherein the positioning control handle part and the ablation control handle part are operable in a first configuration in which the positioning control handle part and the ablation control handle part are operable together, and are operable in a second configuration in which the positioning control handle part and the ablation control handle part are spaced from each other and at least one of the positioning control handle part and the ablation control handle part are operable independently from each other, wherein in the first configuration the positioning catheter is positionable at a defined position in the object and in the second configuration a shape of the ablation catheter is adjustable by movement of the ablation control handle part relative to the positioning control handle part for changing the shape of the ablation catheter from an essentially linear to an essentially loop shaped configuration relative to a longitudinal axis of the ablation catheter and to bring the ablation catheter into contact with a portion of the object to be ablated, wherein the ablation catheter comprises a shape memory material having a substantially loop shaped configuration as a stored shape, and wherein the supply lumina and the draining lumina are attached to the positioning control handle part and the intermediate part so that the supply lumina and the draining lumina slide relative to each other when the positioning control handle part and the ablation control handle part are shifted relative to each other.

18. The method according to claim 17, wherein a pressure control valve is arranged within the draining lumina through which a return path of the exhausted gaseous refrigerant extends.

* * * * *

UNITED STATES PATENT AND TRADEMARK OFFICE
CERTIFICATE OF CORRECTION

PATENT NO. : 9,492,216 B2
APPLICATION NO. : 12/922150
DATED : November 15, 2016
INVENTOR(S) : Gerald Fischer et al.

It is certified that error appears in the above-identified patent and that said Letters Patent is hereby corrected as shown below:

In the Claims

Column 17, Line 54, Claim 1    Delete "through the position",
                               Insert --through the positioning--

Column 17, Line 59, Claim 1    After "draining exhausted cooling agent,",
                               Insert --wherein the positioning control handle part and the
                               ablation control handle part are separable from one another,--

Column 18, Lines 2-4, Claim 1  Delete "each other, is spaced from and operable
                               independently from the other one of the positioning control
                               handle part and the ablation control handle part,",
                               Insert --each other,--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*